(12) United States Patent
Debreczeny et al.

(10) Patent No.: US 8,180,419 B2
(45) Date of Patent: May 15, 2012

(54) TISSUE HYDRATION ESTIMATION BY SPECTRAL ABSORPTION BANDWIDTH MEASUREMENT

(75) Inventors: Martin P. Debreczeny, Danville, CA (US); Clark R. Baker, Jr., Newman, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1631 days.

(21) Appl. No.: 11/528,154

(22) Filed: Sep. 27, 2006

(65) Prior Publication Data

US 2008/0076983 A1    Mar. 27, 2008

(51) Int. Cl.
*A61B 5/1455*    (2006.01)
*A61B 6/00*    (2006.01)

(52) U.S. Cl. .................... 600/310; 600/322; 600/473

(58) Field of Classification Search ............... 600/309, 600/310, 316, 322, 340, 473, 476; 356/301, 356/302
See application file for complete search history.

(56) References Cited

U.S. PATENT DOCUMENTS

| | | | |
|---|---|---|---|
| 3,998,550 A | 12/1976 | Konishi et al. | |
| 4,066,068 A | 1/1978 | Nilsson et al. | |
| 4,364,008 A | 12/1982 | Jacques | |
| 4,711,244 A | 12/1987 | Kuzara | |
| 4,723,554 A | 2/1988 | Oman et al. | |
| 4,805,623 A | 2/1989 | Jobsis | |
| 4,832,483 A * | 5/1989 | Verma ......................... 600/322 | |
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 5,057,695 A | 10/1991 | Hirao et al. | |
| 5,070,874 A * | 12/1991 | Barnes et al. ............. 600/316 | |
| 5,086,781 A | 2/1992 | Bookspan | |
| 5,111,817 A | 5/1992 | Clark et al. | |
| 5,146,091 A | 9/1992 | Knudson | |
| 5,224,478 A | 7/1993 | Sakai et al. | |
| 5,277,181 A | 1/1994 | Mendelson et al. | |
| 5,279,295 A | 1/1994 | Martens et al. | |
| 5,282,467 A | 2/1994 | Piantadosi et al. | |
| 5,337,745 A | 8/1994 | Benaron | |
| 5,337,937 A | 8/1994 | Remiszewski et al. | |
| 5,348,002 A * | 9/1994 | Caro ............................ 600/310 | |
| 5,348,004 A | 9/1994 | Hollub | |

(Continued)

FOREIGN PATENT DOCUMENTS

CA    2353007 A1    6/2000

(Continued)

OTHER PUBLICATIONS

Wheeler, Owen H., "Near Infrared Spectra of Organic Compounds," Department of Chemistry, College of Agriculture and Mechanic Arts, University of Puerto Rico (Mar. 1929).

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

A system and method are provided for determining tissue hydration. Specifically, in accordance with one aspect of the present invention there is provided a method for determining tissue hydration. The method includes detecting electromagnetic radiation scattered and reflected from the living tissue and using the detected electromagnetic radiation to determine spectral absorption bandwidth. The method also includes correlating the spectral absorption bandwidth to a tissue hydration index.

37 Claims, 7 Drawing Sheets

U.S. PATENT DOCUMENTS

| | | | | |
|---|---|---|---|---|
| 5,355,880 | A | 10/1994 | Thomas et al. | |
| 5,377,674 | A | 1/1995 | Kuestner | |
| 5,499,627 | A | 3/1996 | Steuer et al. | |
| 5,533,509 | A * | 7/1996 | Koashi et al. | 600/316 |
| 5,615,689 | A | 4/1997 | Kotler | |
| 5,687,721 | A | 11/1997 | Kuhls | |
| 5,701,902 | A | 12/1997 | Vari et al. | |
| 5,720,284 | A | 2/1998 | Aoyagi et al. | |
| 5,725,480 | A * | 3/1998 | Oosta et al. | 600/310 |
| 5,735,284 | A | 4/1998 | Tsoglin et al. | |
| 5,747,789 | A | 5/1998 | Godik | |
| 5,755,672 | A | 5/1998 | Arai et al. | |
| 5,788,643 | A | 8/1998 | Feldman | |
| 5,792,050 | A * | 8/1998 | Alam et al. | 600/310 |
| 5,803,908 | A | 9/1998 | Steuer et al. | |
| 5,827,181 | A | 10/1998 | Dias et al. | |
| 5,833,602 | A | 11/1998 | Osemwota | |
| 5,851,178 | A * | 12/1998 | Aronow | 600/323 |
| 5,853,364 | A | 12/1998 | Baker, Jr. et al. | |
| 5,860,919 | A | 1/1999 | Kiani-Azarbayjany et al. | |
| 5,906,582 | A | 5/1999 | Kondo et al. | |
| 6,064,898 | A | 5/2000 | Aldrich | |
| 6,125,297 | A | 9/2000 | Siconolfi | |
| 6,149,591 | A | 11/2000 | Henderson et al. | |
| 6,178,342 | B1 | 1/2001 | Thompson et al. | |
| 6,222,189 | B1 | 4/2001 | Misner et al. | |
| 6,246,894 | B1 | 6/2001 | Steuer et al. | |
| 6,280,396 | B1 | 8/2001 | Clark et al. | |
| 6,336,044 | B1 | 1/2002 | Ghiassi et al. | |
| 6,370,426 | B1 | 4/2002 | Campbell et al. | |
| 6,400,971 | B1 | 6/2002 | Finarov et al. | |
| 6,402,690 | B1 | 6/2002 | Rhee et al. | |
| 6,442,408 | B1 | 8/2002 | Wenzel et al. | |
| 6,453,183 | B1 * | 9/2002 | Walker | 600/322 |
| 6,466,807 | B1 | 10/2002 | Dobson et al. | |
| 6,488,677 | B1 | 12/2002 | Bowman et al. | |
| 6,512,936 | B1 | 1/2003 | Monfre et al. | |
| 6,587,701 | B1 * | 7/2003 | Stranc et al. | 600/310 |
| 6,591,122 | B2 | 7/2003 | Schmitt | |
| 6,592,574 | B1 | 7/2003 | Shimmick et al. | |
| 6,600,946 | B1 | 7/2003 | Rice | |
| 6,606,509 | B2 | 8/2003 | Schmitt | |
| 6,615,064 | B1 | 9/2003 | Aldrich | |
| 6,635,491 | B1 | 10/2003 | Khalil et al. | |
| 6,636,759 | B2 | 10/2003 | Robinson | |
| 6,643,543 | B2 | 11/2003 | Takehara et al. | |
| 6,654,620 | B2 | 11/2003 | Wu et al. | |
| 6,668,181 | B2 | 12/2003 | Wenzel et al. | |
| 6,675,029 | B2 | 1/2004 | Monfre et al. | |
| 6,687,519 | B2 | 2/2004 | Steuer et al. | |
| 6,697,652 | B2 * | 2/2004 | Georgakoudi et al. | 600/310 |
| 6,777,240 | B2 | 8/2004 | Hazen et al. | |
| 6,849,046 | B1 | 2/2005 | Eyal-Bickels | |
| 6,873,865 | B2 | 3/2005 | Steuer et al. | |
| 6,882,874 | B2 | 4/2005 | Huiku et al. | |
| 6,950,699 | B1 | 9/2005 | Manwaring et al. | |
| 6,961,598 | B2 | 11/2005 | Diab | |
| 7,215,991 | B2 | 5/2007 | Besson et al. | |
| 7,277,741 | B2 | 10/2007 | Debreczeny et al. | |
| 7,283,242 | B2 | 10/2007 | Thornton | |
| 7,343,186 | B2 | 3/2008 | Lamego et al. | |
| 2001/0020122 | A1 | 9/2001 | Steuer et al. | |
| 2003/0060693 | A1 | 3/2003 | Monfre et al. | |
| 2004/0127777 | A1 | 7/2004 | Richti et al. | |
| 2004/0147034 | A1 | 7/2004 | Gore et al. | |
| 2004/0230106 | A1 | 11/2004 | Schmitt et al. | |
| 2005/0119538 | A1 | 6/2005 | Jeon et al. | |
| 2005/0267346 | A1 | 12/2005 | Faber et al. | |
| 2006/0020181 | A1 | 1/2006 | Schmitt | |
| 2006/0052680 | A1 | 3/2006 | Diab et al. | |
| 2006/0084864 | A1 | 4/2006 | Schmitt et al. | |
| 2006/0167350 | A1 | 7/2006 | Monfre et al. | |
| 2006/0276696 | A1 | 12/2006 | Schurman | |
| 2007/0078311 | A1 | 4/2007 | Al-Ali et al. | |
| 2007/0167693 | A1 | 7/2007 | Scholler et al. | |
| 2007/0282178 | A1 | 12/2007 | Scholler et al. | |
| 2007/0282183 | A1 | 12/2007 | Scholler et al. | |
| 2008/0004513 | A1 | 1/2008 | Walker et al. | |
| 2008/0097173 | A1 | 4/2008 | Soyemi et al. | |
| 2008/0154104 | A1 | 6/2008 | Lamego et al. | |

FOREIGN PATENT DOCUMENTS

| | | | |
|---|---|---|---|
| DE | 19855521 | A1 | 6/2000 |
| EP | 1135184 | A1 | 6/2000 |
| EP | 1184663 | A2 | 3/2002 |
| FR | 2710517 | | 4/1995 |
| JP | 4-40940 | | 2/1992 |
| JP | 5-329163 | | 12/1993 |
| JP | 11-244266 | | 9/1999 |
| JP | 2004 081427 | A | 3/2004 |
| JP | 25169020 | | 6/2005 |
| JP | 25278758 | | 10/2005 |
| JP | 26075354 | | 3/2006 |
| WO | WO 93/13706 | A2 | 7/1993 |
| WO | WO 95/19562 | A | 7/1995 |
| WO | WO 98/34097 | | 8/1998 |
| WO | WO 00/32262 | A1 | 6/2000 |
| WO | WO 00/71025 | A1 | 11/2000 |
| WO | WO 01/16577 | A1 | 3/2001 |
| WO | WO 03/010510 | A | 2/2003 |
| WO | WO 2005/041765 | A | 5/2005 |

OTHER PUBLICATIONS

Pace, Nello et al., "Studies on Body Composition: III. The body water and chemically combined nitrogen content in relation to fat content," Naval Medical Research Institute, Bethesda, Maryland (Jan. 11, 1945).

Mitchell, H. M. et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).

Schloerb, Paul R. et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M. et al., "The Composition of the Adult Human Body as Determined by Chemical Analysis," Division of Animal Nutrition, and the Department of Anatomy, University of Illinois, Jan. 19, 1953.

Buijs, K. et al., "Near-Infrared Studies of the Structure of Water. I. Pure Water," *The Journal of Chemical Physics*, vol. 39, No. 8, pp. 2035-2041 (Oct. 15, 1963).

Choppin, G.R. et al., "Near-Infrared Studies of the Structure of Water. II. Ionic Solutation," *The Journal of Chemical Physics*, vol. 39, No. 8, pp. 2042-2050 (Oct. 15, 1963).

Goldstein, R. et al., "The Near-Infrared Absorption of Liquid Water at Temperatures Between 27 and 209°C.," *J. Quant. Spectrosc. Radiat. Transfer.*, vol. 4, pp. 441-451 (1964).

Ben-Gera, I. et al., "Influence of Fat Concentration on the Absorption Spectrum of Milk in the Near-Infrared Region," *Israel J. Agric. Res.*, vol. 18, No. 3, pp. 117-124 (Jul. 1968).

Houseman, R.A. et al., "The measurement of total body water in living pigs by deuterium oxide dilution and its relation to body composition," *Br. J. Nutr.*, vol. 30, pp. 149-156 (1973).

Krikorian, S. Edward et al., "The identification and origin of N-H overtone and combination bands in the near-infrared spectra of simple primary and secondary amides," *Spectrochimica Acta*, vol. 29A, pp. 1233-1246 (1973).

Lesser, G.T. et al., "Body water compartments with human aging using fat-free mass as the reference standard," *Am J. Physiol Regul Integr Comp Physiol.*, vol. 236, pp. 215-220 (1979).

Sheng, Hwai-Ping et al., "A review of body composition studies with emphasis on total body water and fat," *The American Journal of Clinical Nutrition*, vol. 32., pp. 630-647 (Mar. 1979).

Martens, H. et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J. et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," *Journal of Food Science*, vol. 48, pp. 471-474 (1983).

Martens, Harald et al., "Understanding food research data," Food Research and Data Analysis, Applied Science Publishers, pp. 5-38 (1983).

Shields, R. G., Jr. et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Cohn, S.H. et al., "Assessment of cellular mass and lean body mass by noninvasive nuclear techniques," *J. Lab Clin Med.*, vol. 105, pp. 305-311 (1985).

Hannon, John P. et al., "Splenic red cell sequestration and blood volume measurements in conscious pigs," *Am J. Physiol.*, vol. 248, pp. R293-R301 (1985).

Potts, R.O. et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Cox, Patrick et al., "Variations in Lipids in Different Layers of Porcine Epidermis," *J. Invest Dermatol.*, vol. 87, pp. 741-744 (1986).

Valdes, E. V. et al., "Determination of Crude Protein and Fat in Carcass and Breast Muscle Samples of Poultry by Near Infrared Reflectance Spectroscopy," *Poultry Science*, vol. 65, pp. 485-490 (1986).

Hedberg, Chrisopher L. et al., "The Time Course of Lipid Biosynthesis in Pig Epidermis," *J. Invest Dermatol.*, vol. 91, pp. 169-174 (1988).

Hedberg, Christopher L. et al., "The nonpolar Lipids of Pig Epidermis," *J. Invest Dermatol.*, vol. 90, pp. 225-229 (1988).

Trapp, Scott A. et al., "An improved spectrophotometric bromide assay for the estimation of extracellular water volume," *Clinica Chimica Acta.*, vol. 181, pp. 207-212, (1989).

Bommannan, D. et al., "Examination of Stratum Corneum Barrier Function In Vivo by Infrared Spectroscopy," *J. Invest Dermatol*, vol. 95, pp. 403-408 (1990).

Hannon, John P. et al., "Normal Physiological Values for Conscious Pigs Used in Biomedical Research," *Laboratory Animal Science*, vol. 40, No. 3, May 1990.

Mak, Vivien H.W. et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Drummer, C. et al., "Effects of an acute saline infusion on fluid and electrolyte metabolism in humans," *Am J. Physiol.*, vol. 262, pp. F744-F754 (1992).

Horber, F.F. et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E. et al., "Near infrared calibrations for goat's milk components; protein, total casein, $\alpha_s$-, $\beta$- and $\kappa$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M. et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J. et al., "Absolute quantification of deoxyhaemoglobin concentration in tissue near infrared spectroscopy," *Phys. Med. Biol.*, vol. 39, pp. 1295-1312 (1994).

Simanonok, Karl E. et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C. et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-4272.

Warren, Joan L. et al., "The Burden and Outcomes Associates with Dehydration among US Elderly, 1991," *American Journal of Public Health*, vol. 84, No. 8, pp. 1265-1269 (Aug. 1994).

Åneman, Anders et al., "Splanchnic and Renal Sympathetic Activity in Relation to Hemodynamics During Isoflurane Administration in Pigs," *Anesth Analg.*, vol. 80, pp. 135-142, (1995).

Kisch, Hille et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N. et al., "Prediction of Tissular Body Composition from Protein and Lipid Deposition in Growing Pigs," *J. Anim. Sci.*, vol. 73, pp. 1567-1575, (1995).

Avis, N.J. et al.; "In vitro multifrequency electrical impedance measurements and modeling of the cervix in late pregnancy", *Physiological Measurement*, vol. 17, pp. A97-A103, 1996.

Gniadecka, M. et al., "Assessment of dermal water by high-frequency ultrasound: comparative studies with nuclear magnetic resonance," *British Journal of Dermatology*, vol. 135, pp. 218-224, (1996).

Finn, Patrick J. et al., "Progressive cellular dehydration and proteolysis in critically ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P. et al.; "Prediction of body cell mass, fat-free mass, and total body water with bioelectrical impedance analysis: effects of race, sex, and disease;" *Am J. Clin. Nutr*. 64(suppl):489S-97S (1996).

Kumar, Gitesh et al., "Non-Invasive Optical Assessment of Tissue Hydration," *International Conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M. et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo et al., "Hemodilution, central blood volume, and renal responses after an isotonic saline infusion in humans," *Am J. Physiol.*, vol. 272, pp. R549-R556 (1997).

Visser, Marjolein et al., "Density of fat-free body mass: relationship with race, age, and level of body fatness," *Am J. Physiol.*, vol. 272, pp. E781-E787, (1997).

Alanen, Esko et al., "Measurement of dielectric properties of subcutaneous fat with open-ended coaxial sensors," *Phys. Med. Biol.*, vol. 43, pp. 475-485 (1998).

Alanen, Esko et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C. et al., "Role of Tissue-Specific Blood Flow and Tissue Recruitment in Insulin-Mediated Glucose Uptake of Human Skeletal Muscle," *Circulation*, vol. 98, pp. 234-241, (1998).

Bracco, David et al., "Bedside determination of fluid accumulation after cardiac surgery using segmental bioelectrical impedance," *Crit Care Med*, vol. 26, No. 6, pp. 1065-1070 (1998).

Gniadecka, Monika et al., "Water and Protein Structure in Photoaged and Chronically Aged Skin," *J. Invest Dermatol*, vol. 111, pp. 1129-1133 (1998).

Gniadecka, Monika et al., "Structure of Water, Proteins, and Lipids in Intact Human Skin, Hair, and Nail," *J. Invest Dermatol*, vol. 110, pp. 393-398 (1998).

Gow, Kenneth W. et al., "Effect of crystalloid administration on oxygen extraction in endotoxemic pigs," *J. Appl. Physiol.*, vol. 85, No. 5, pp. 1667-1675 (1998).

Husby, P. et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D. et al., "Composition Analysis of Pork Carcasses by Dual-Energy X-Ray Absorptiometry," *J. Anim. Sci.*, vol. 76, pp. 2104-2114 (1998).

Mahan, D. C. et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning et al., "Uncompensated Blood Loss is Not Tolerated During Acute Normovolemic Hemodilution in Anesthetized Pigs," *Anesth Analg.*, vol. 87, pp. 786-794 (1998).

Stranc, M.F. et al., "Assessment of tissue viability using near-infrared spectroscopy," *British Journal of Plastic Surgery*, vol. 51, pp. 210-217, (1998).

Thomas, B. J. et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette et al., "Biochemistry of tropoelastin," *Eur. J. Biochem.*, vol. 258, pp. 1-18 (1998).

Alanen, Esko et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C. et al., "Reliability and validity of body composition measures in female athletes," Journal of Applied Physiology, vol. 87, pp. 1114-1122, (1999).

Fusch, Christoph et al., "Neonatal Body Composition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R. et al., "Single- and multifrequency models for bioelectrical impedance analysis of body water compartments," *J. Appl. Physiol.*, vol. 87, No. 3, pp. 1087-1096 (1999).

Jennings, Graham et al., "The Use of infrared Spectrophotometry for Measuring Body Water Spaces," vol. 45, No. 7, pp. 1077-1081 (1999).

Kalantar-Zadeh, Kamyar et al., "Near infra-red interactance for nutritional assessment of dialysis patients," *Nephrol Dial Transplant*, vol. 14, pp. 169-175 (1999).

Kayser-Jones, Jeanie et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R. et al., "The measurement of lung water," *Critical Care*, vol. 3, pp. R19-R24 (1999).

Van Marken Lichtenbelt, Wouter D. et al., "Increased extracellular water compartment, relative to intracellular water compartment, after weight reduction," *Journal of Applied Physiology*, vol. 87, pp. 294-298 (1999).

Rennie, Michael J., "Perspectives—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R. et al., "Analysis of Body Composition Changes of Swine During Growth and Development," *J. Anim. Sci.*, vol. 77, pp. 1442-1466 (1999).

Wang, Zimian et al., "Hydration of fat-free body mass: new physiological modeling approach," *Am. J. Physiol.*, vol. 276, pp. E995-E1003 (1999).

Wang, Zimian et al., "Hydration of fat-free body mass: review and critique of a classic body-composition constant," *Am J. Clin. Nutr.*, vol. 69, pp. 833-841 (1999).

Ward, L. et al., "Multiple frequency bioelectrical impedance analysis: a cross-validation study of the inductor circuit and Cole models," Physiol. Meas., vol. 20, pp. 333-347 (1999).

Wells, Jonathan CK et al., "Four-component model of body composition in children: density and hydration of fat-free mass and comparison with simpler models," *Am J. Clin. Nutr.*, vol. 69, pp. 904-912 (1999).

Butte, Nancy F. et al., "Body Composition during the First 2 Years of Life; An Updated Reference," *Pediatric Research*, vol. 47, No. 5, pp. 578-585 (2000).

Feigenbaum, Matthew S. et al., "Contracted Plasma and Blood Volume In Chronic Heart Failure," *J Am Coll. Cardiol.*, vol. 35, No. 1, pp. 51-55 (Jan. 2000).

Kays, Sandra E. et al., "Predicting protein content by near infrared reflectance spectroscopy in diverse cereal food products," *J. Near Infrared Spectrosc.*, vol. 8, pp. 35-43 (2000).

Lucassen, G. et al., "Water Content and Water Profiles in Skin Measured by FTIR and Raman Spectroscopy," *Proc. SPIE*, vol. 4162, pp. 39-45 (2000).

Plank, L. D. et al., "Similarity of Changes in Body Composition in Intensive Care Patients following Severe Sepsis or Major Blunt Injury," *Annals New York Academy of Sciences*, pp. 592-602 (2000).

Ritz, P. et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R. et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael et al., "Visualization of cutaneous hemoglobin oxygenation and skin hydration using near-infrared spectroscopic imaging," *Skin Research and Technology*, vol. 7, pp. 238-245, (2001).

Bray, George A. et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W. et al., "The Recommended Dietary Allowance for Protein May Not Be Adequate for Older People to Maintain Skeletal Muscle," *Journal of Gerontology*, vol. 56A, No. 6, pp. M373-M-380 (2001).

Divert, Victor E., "Body Thermal State Influence on Local Skin Thermosensitivity," *International Journal of Circumpolar Health*, vol. 60, pp. 305-311 (2001).

Du, Y. et al., "Optical properties of porcine skin dermis between 900 nm and 1500 nm," *Phys. Med. Biol.*, vol. 46, pp. 167-181 (2001).

Endo, Yutaka et al., "Water drinking causes a biphasic change in blood composition in humans," Pflügers Arch—Eur J. Physiol, vol. 442, pp. 362-368 (2001).

Garaulet, Marta et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A. et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar et al., "Near infra-red interactance for Longitudinal Assessment of Nutrition in Dialysis Patients," *Journal of Renal Nutrition*, vol. 11, No. 1, pp. 23-31 (Jan. 2001).

Kamba, Masayuki et al., "Proton magnetic resonance spectroscopy for assessment of human body composition," *Am J. Clin. Nutr.*, vol. 73, pp. 172-176 (2001).

Lever, M. et al., "Some ways of looking at compensatory kosmotropes and different water environments," *Comparative Biochemistry and Physiolog.*, vol. 130, Part A, pp. 471-486, (2001).

Mingrone, G. et al., "Unreliable use of standard muscle hydration value in obesity," *Am J. Physiol Endocrinal Metab.*, vol. 280, pp. E365-E371, (2001).

Šašic, Slobodan et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P. et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Troy, Tamara L. et al., "Optical properties of human skin in the near infrared wavelength range of 1000 to 2200nm," *Journal of Biomedical Optics*, vol. 6, No. 2, pp. 167-176 (Apr. 2001).

Tsukahara, K. et al., "Dermal fluid translocation is an important determinant of the diurnal variation in human skin thickness," *British Journal of Dermatology*, vol. 145, pp. 590-596 (2001).

Vescovi, Jason D. et al., "Evaluation of the BOD POD for estimating percentage body fat in a heterogeneous group of adult humans," *Eur J. Appl. Physiol.*, vol. 85, pp. 326-332 (2001).

Wang, Zimian et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B. et al., "Clinical Results from a Non-Invasive Blood Glucose Monitor," *Photonics West 2002 Meeting*, San Jose, California, Jan. 19-25, 2002 (25 pages).

Chamney, Paul W. et al., "A new technique for establishing dry weight in hemodialysis patients via whole body bioimpedance," *Kidney International*, vol. 61, pp. 2250-2258 (2002).

Drobin, Dan et al., "Kinetics of Isotonic and Hypertonic Plasma Volume Expanders," *Anesthesiology*, vol. 96, No. 6, pp. 1371-1380 (Jun. 2002).

Endo, Yutaka et al., "Changes in Blood Pressure and Muscle Sympathetic Nerve Activity during Water Drinking in Humans," *Japanese Journal of Physiology*, vol. 52, pp. 421-427 (2002).

Haga, Henning A. et al., "Motor responses to stimulation during isoflurane anaesthesia in pigs," *Veterinary Anaesthesia and Analgesia*, vol. 29, pp. 69-75 (2002).

Klaus, Stephan et al., "Assessment of fluid balance by measurement of skin tissue thickness during clinical anaesthesia," *Clin. Physiol. & Func. Im.*, vol. 22, pp. 197-201 (2002).

Meglinski, Igor V. et al., "Quantitative assessment of skin layers absorption and skin reflectance spectra simulation in the visible and near-infrared spectral regions," *Physiol. Meas.*, vol. 23, pp. 741-753, (2002).

Perez-de-Sá, Valéria et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria et al., "Characterization of Reconstructed Skin Models," *Skin Pharmacol Appl Skin Physiol.*, vol. 15, Supplement 1, pp. 4-17, (2002).

Querleux, B. et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W. et al., "Evaluating body fat in girls and female adolescents: advantages and disadvantages of dual-energy X-ray absorptiometry," *Am J. Clin Nutr.*, vol. 76, pp. 384-389 (2002).

Baković, Darija et al., "Spleen volume and blood flow response to repeated breath-hold apneas," *J. Appl. Physiol.*, vol. 95, pp. 1460-1466 (2003).

Bartok, Cynthia et al., "Measurement of nutritional statusin simulated microgravity by bioelectrical impedance spectroscopy," *J. Appl. Physiol.*, vol. 95, pp. 225-232 (2003).

Bouwstra, Joke A. et al., "Water Distribution and Related Morphology in Human Stratum Corneum at Different Hydration Levels," *J. Invest Dermatol*, vol. 150, pp. 750-758 (2003).

Butte, Nancy F. et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach or Not to Teach, That is the Question—Intravenous Fluid Resuscitation Training for Combat Lifesavers," *The Journal of TRAUMA, Injury, Infection, and Critical Care*, vol. 54, No. 5, pp. S20-S25 (May Supplement 2003).

Cook, Lynda S., "IV Fluid Resuscitation," *Journal of Infusion Nursing*, vol. 26, No. 5, pp. 296-303 (Sep./Oct. 2003).

Dey, D.K. et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M. et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the 21$^{st}$ century", *Nutrition Reviews*, 61(8):261-271 (2003).

Heise, H.M. et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Kemming, G.I. et al., "Hyperoxic ventilation at the critical haematocrit," *Resuscitation*, vol. 56, pp. 289-297 (2003).

Kurita, T. et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu et al., "Study of Novel Chitosan-gelatin artificial skin in vitro," *J. Miomed Mater Res.*, vol. 64, Part A, pp. 301-308 (2003).

Mauran, P. et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, Letter "Passive leg elevation and head-down tilt: effects and duration of changes," *Critical Care*, vol. 7, No. 3, p. 246 (Jun. 2003).

Meglinski, I.V. et al., "Computer simulation of the skin reflectance spectra," *Computer Methods and Programs in Biomedicine*, vol. 70, pp. 179-186, (2003).

Mendelsohn, Richard et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C. et al., "Reducing Hydration-Linked events in Nursing Home Residents," *Clinical Nursing Research*, vol. 12, No. 3, pp. 210-225 (Aug. 2003).

Merritt, Sean et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa et al., "Validity of Six Field and Laboratory Methods for Measurement of Body Composition in Boys," *Obesity Research*, vol. 11, No. 7, pp. 852-858 (Jul. 2003).

Petäjä L. et al., "Dielectric constant of skin and subcutaneous fat to assess fluid changes after cardiac surgery", *Physiological Measurement*, 24: 3383-390, 2003.

Rhodes, Andrew et al., "Book Report—Haemodynamic monitoring in critically ill patients," *Critical Care*, vol. 8, p. 203 (2004).

Richardson, Andrew D. et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Ritz, Patrick, "Chronic Cellular Dehydration in the Aged Patient," Journal of Gerontology, vol. 56A, No. 6, pp. M349-M352 (2001).

Robinson, Martin P. et al., "A novel method of studying total body water content using a resonant cavity: experiments and numerical simulation," *Phys. Med. Biol.*, vol. 48, pp. 113-125, (2003).

Sergi, Giuseppe et al., "Changes in Fluid Compartments and Body Composition in Obese Women after Weight Loss Induced by Gastric Banding," *Ann. Nutr Metab.*, vol. 47., pp. 152-157 (2003).

Wang, Zimian et al., "Magnitude and variation of fat-free mass density: a cellular level body composition modeling study," *Am J. Physiol. Endocrinal. Metab*, vol. 284, pp. E267-E273 (2003).

Windberger, U et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L. et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R. et al., "A review of the literature on how important water is to the world's elderly population," *International Nursing Review*, vol. 51, pp. 159-166 (2004).

Dullenkopf, A. et al., "Non-invasive monitoring of haemoglobin concentration in paediatric surgical patients using near-infrared spectroscopy," *Anaesthesia*, vol. 59, pp. 453-458 (2004).

Finlay, Jarod C. et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M. et al., "Influence of hydration and experimental length scale on the mechanical response o human skin in vivo, using optical coherence tomography," *Skin Research and Technology*, vol. 10, pp. 231-241 (2004).

Hieda, I. et al., "Basic characteristics of the radio imaging method for biomedical application," *Medical Engineering & Physics*, vol. 26, pp. 431-437 (2004).

Ikizler, T. Alp et al., "Urea space and total body water measurements by stable isotopes in patients with acute renal failure," *Kidney International*, vol. 65, pp. 725-732 (2004).

Isenring, E. et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute et al., "In vivo determination of skin surface topography using an optical 3D device," *Skin Research and Technology*, vol. 10, pp. 207-214 (2004).

Kao, Bunsho et al., "Evaluation of Cryogen Spray Cooling Exposure on In Vitro Model Human Skin," *Lasers in Surgery and Medicine*, vol. 34, pp. 146-154 (2004).

Kyle, Urusula G. et al., "Bioelectrical impedance analysis—part II: utilization in clinical practice," *Clinical Nutrition*, vol. 23, pp. 1430-1453 (2004).

Lof, Marie et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F. et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh et al., "In vivo morphological characterization of skin by MRI micro-imaging methods," *Skin Research and Technology*, vol. 10, pp. 149-160, (2004).

Notingher, Ioan et al., "Mid-infrared in vivo depth-profiling of topical chemicals on skin," *Skin Research and Technology*, vol. 10, pp. 113-121, (2004).

Nouveau-Richard, S. et al., "In vivo epidermal thickness measurement: ultrasound vs. confocal imaging," *Skin Research and Technology*, vol. 10, pp. 136-140, (2004).

Nuutinen, J. et al., "Validation of a new dielectric device to assess changes of tissue water in skin and subcutaneous fat," *Physiol. Meas.*, vol. 25, pp. 447-454, (2004).

St-Onge, Marie-Pierre et al., "Dual-energy X-ray absorptiometry lean soft tissue hydration: independent contributions of intra- and extracellular water," *Am J. Physiol. Endrocrinol Metab*, vol. 287, pp. E842-E847, Jul. 6, 2004.

Schou, A. J. et al., "Methodological aspects of high-frequency ultrasound of skin in children," *Skin Research and Technology*, vol. 10, pp. 200-206, (2004).

Stone, Darren A. et al., "Total body water measurements using resonant cavity perturbation techniques," *Phys. Med. Biol.*, vol. 49, pp. 1773-1788, (2004).

Takiwaki, Hirotsugu et al., "Analysis of the absorbance spectra of skin lesions as a helpful tool for detection of major pathophysiological changes," *Skin Research and Technology*, vol. 10, pp. 130-135 (2004).

Van Kemenade, Patricia M. et al., "Do somotic forces play a role in the uptake of water by human skin?", *Skin Research and Technology*, vol. 10, pp. 109-112 (2004).

Wang, Zimian et al., "Body cell mass: model development and validation at the cellular level of body composition," *Am J. Physiol. Endocrinol. Metab.*, vol. 286, pp. E123-E128 (2004).

Arimoto, Hidenobu et al., "Depth profile of diffuse reflectance near-infrared spectroscopy for measurement of water content in skin," *Skin Research and Technology*, vol. 11, pp. 27-35 (2005).

Burmeister, J.J. et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D. et al., "Composition of the fat-free mass in obese and nonobese children: matched case—control analyses," *International Journal of Obesity*, vol. 29, pp. 29-36 (2005).

Ivorra, Antoni et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R. et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K. et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.pdf (last accessed, Nov. 30, 2005).

García-Olmo, J. et al., "Advantages and disadvantages of multiple linear regression and partial least squares regression equations for the prediction of fatty acids," pp. 253-258 (undated).

Wang, Zimian et al., "Cellular-Level Body Composition Model—A New Approach to Studying Fat-free Mass Hydration," *Annals New York Academy of Sciences*, pp. 306-311 (undated).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

L. Liu, et al.; "Estimating Winter Wheat Plant Water Conent Using Red Edge Width," *IGARSS 2003—IEEE 2003 International Geoscience and Remote Sensing Symposium Proceedings*, Toulouse, France (Jul. 21-25, 2003); *IEEE International Geoscience and Remote Sensing Symposium*, New York, NY, vol. 7 of 7 (Jul. 21, 2003); pp. 1688-1691.

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

\* cited by examiner

TISSUE HYDRATION ESTIMATION BY SPECTRAL ABSORPTION BANDWIDTH MEASUREMENT

TECHNICAL FIELD

The present invention relates generally to determining physiological parameters and, more particularly, to determining tissue hydration.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In healthy individuals, homeostatic control mechanisms ensure that a balance between fluid gain and fluid loss is maintained. Therefore, maintaining fluid balance is typically not an issue requiring attention. In ill individuals, however, the maintenance of body fluid balance may be cause for great concern. For example, dehydration or edema may occur if fluid balance is not properly maintained. Dehydration of infants and children suffering from diarrhea and/or vomiting can be life threatening if not recognized and treated promptly. Additionally, individuals with congestive heart failure frequently suffer from edema which must be controlled in order to ensure adequate tissue perfusion and to prevent electrolyte disturbances. Also, over-administration of intravenous fluids in critically ill or surgical patients may result in lung edema, with resulting impairment of gas exchange.

Tissue hydration estimation using a hydration index, such as a ratio of water to the sum of water and protein, provides an accurate, objective and non-invasive way to measure fluid balance. Methods for measuring water in tissue by near-infrared (NIR) spectrophotometry have been described in the art. Previous attempts at using a hydration index, however, have been focused on measuring absorption features of the various tissue constituents. Additionally, the previous attempts have required a minimum of two wavelengths to measure the absorbance contributions of water and protein, and at least a third wavelength to compensate for the effect of tissue scattering. If measurements are made at wavelengths where lipids or other constituents, such as hemoglobin, contribute substantially to the absorption spectrum, a fourth or more wavelengths may be used to measure the hydration index accurately. Each additional wavelength increases cost and complexity of the system.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a method for determining tissue hydration. The method includes detecting electromagnetic radiation scattered and reflected from the living tissue and using the detected electromagnetic radiation to determine the bandwidth of a spectral absorption feature. The method also includes correlating the absorption bandwidth to a tissue hydration index.

In accordance with another aspect of the present invention there, is provided a system for measurement of living tissue. The system includes a sensor unit configured to emit and detect electromagnetic radiation. The system also includes a hydration index unit coupled to the sensor unit. The hydration index unit is configured to determine absorption bandwidth and correlate the absorption bandwidth to living tissue hydration.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
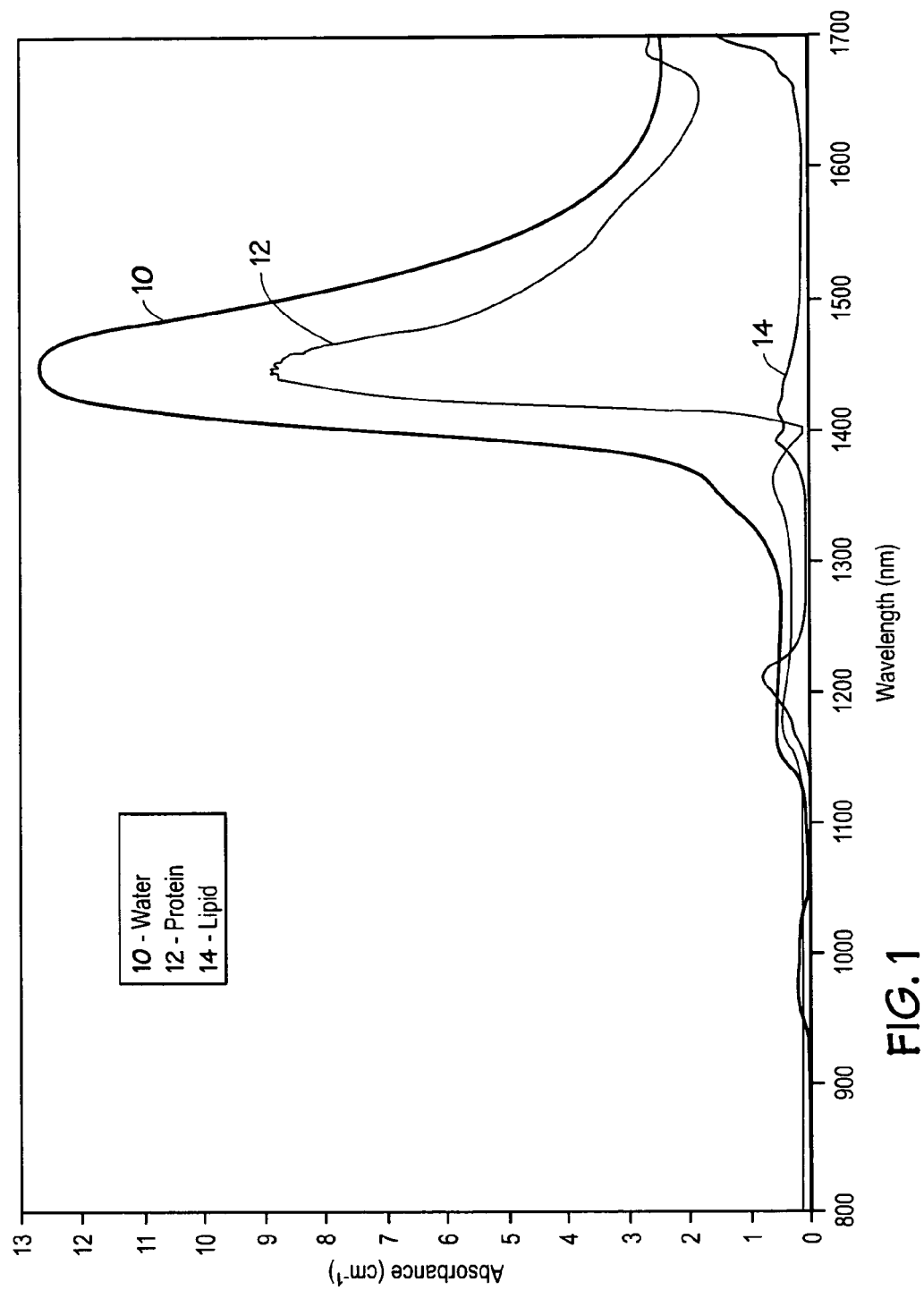
FIG. 1 illustrates plots of the absorbance spectra of the principal components in tissue.

Near Infrared (NIR) absorbance spectra of three major constituents of tissue are shown overlaid in FIG. 1. Specifically, the absorbance spectra of water 10, protein 12 and lipid 14 are shown. As can be seen, the absorbance spectra plots of water 10 and protein 12 have spikes near 1450 nm, while the lipid plot 14 is relatively flat.

Figure 2:
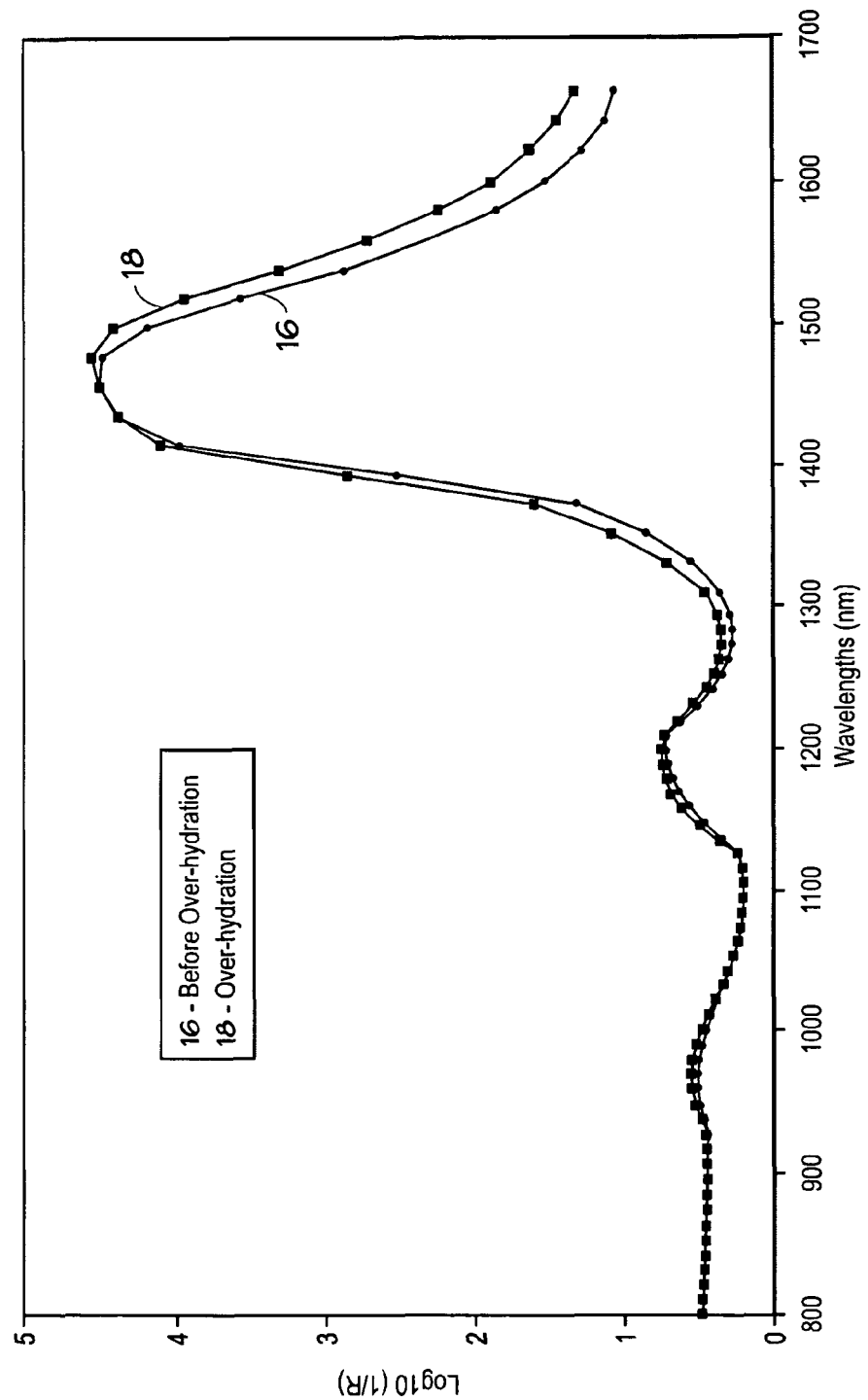
FIG. 2 illustrates plots of the averaged reflectance spectrum before and after over-hydration of piglets in vivo.

Referring to FIG. 2, spectra acquired before and after over-hydration on the torso of a piglet is illustrated. Specifically, the plot 16 is the average spectrum before over-hydration and plot 18 shows the spectrum after over-hydration of five piglets. The piglets were over-hydrated using Lactated Ringer's Solution over the course of six hours by approximately 25% of initial body weight. Given the similarity of the features in FIGS. 1 and 2, it may be possible to determine the relative concentrations of each of the tissue constituents in vivo by matching a linear combination of the constituent spectra to the in vivo spectrum. This simple approach, however, is complicated by the fact that tissue strongly scatters light. The scattering causes a change in the offset as well as the effective path length of light through the tissue as a function of wavelength. In addition, the interaction between the water and the other tissue constituents leads to perturbation of the water spectrum, that cannot by modeled by simply summing the absorbance spectra of pure water with that of the other pure tissue constituents.

A number of theoretical scattering models have been applied to tissue spectra in order to allow the estimation of constituent spectra. Methods for measuring water in tissue by NIR spectroscopy are described in U.S. Pat. No. 6,591,122, U.S. Pub. No. 2003-0220548, and U.S. Pub. No. 2004-0230106, all of which are incorporated herein by reference. However, these techniques are directed to measuring the absorption features of the various tissue constituents and require at least three wavelengths to compensate for the effects of tissue scattering.

In accordance with the present technique, a method and apparatus are provided to estimate analyte concentration through a spectral absorption bandwidth measurement. Specifically, a method and apparatus for determining a whole body hydration index using spectral absorption bandwidth is disclosed. The technique correlates the spectral absorption bandwidth of the water absorption band centered at 1450 nm with whole body hydration and is capable of estimating a hydration index with less than one percent error using only two narrowband light sources, such as light emitting diodes (LEDs).

Near-infrared (NIR) spectroscopic studies of in vivo piglets undergoing hydration changes indicate that the spectral bandwidth of the water absorption band centered at 1450 nm is strongly correlated with whole body hydration. The studies have shown that perturbations of the absorption bandwidth of water occur according to the relative concentration of tissue constituents. For example, lipid concentration has been shown to have a strong effect on the absorption bandwidth. As the concentration of lipid-to-water increases, the absorption bandwidth becomes narrower and the peak is blue-shifted, indicating a decrease in hydration. Additionally, as described above, the plots 16 and 18 illustrate the opposite effect caused by over-hydration. As can be seen, over-hydration causes a broadening and red-shifting of the peak centered at 1450. Accordingly, the absorption bandwidth of water can be correlated to a hydration index indicative of the relative concentrations of constituents of tissue. For example, a hydration index derived from the spectral bandwidth measurement relating to the ratio of water-to-water and other constituents based on the spectral bandwidth of the water absorption band.

Figure 3:
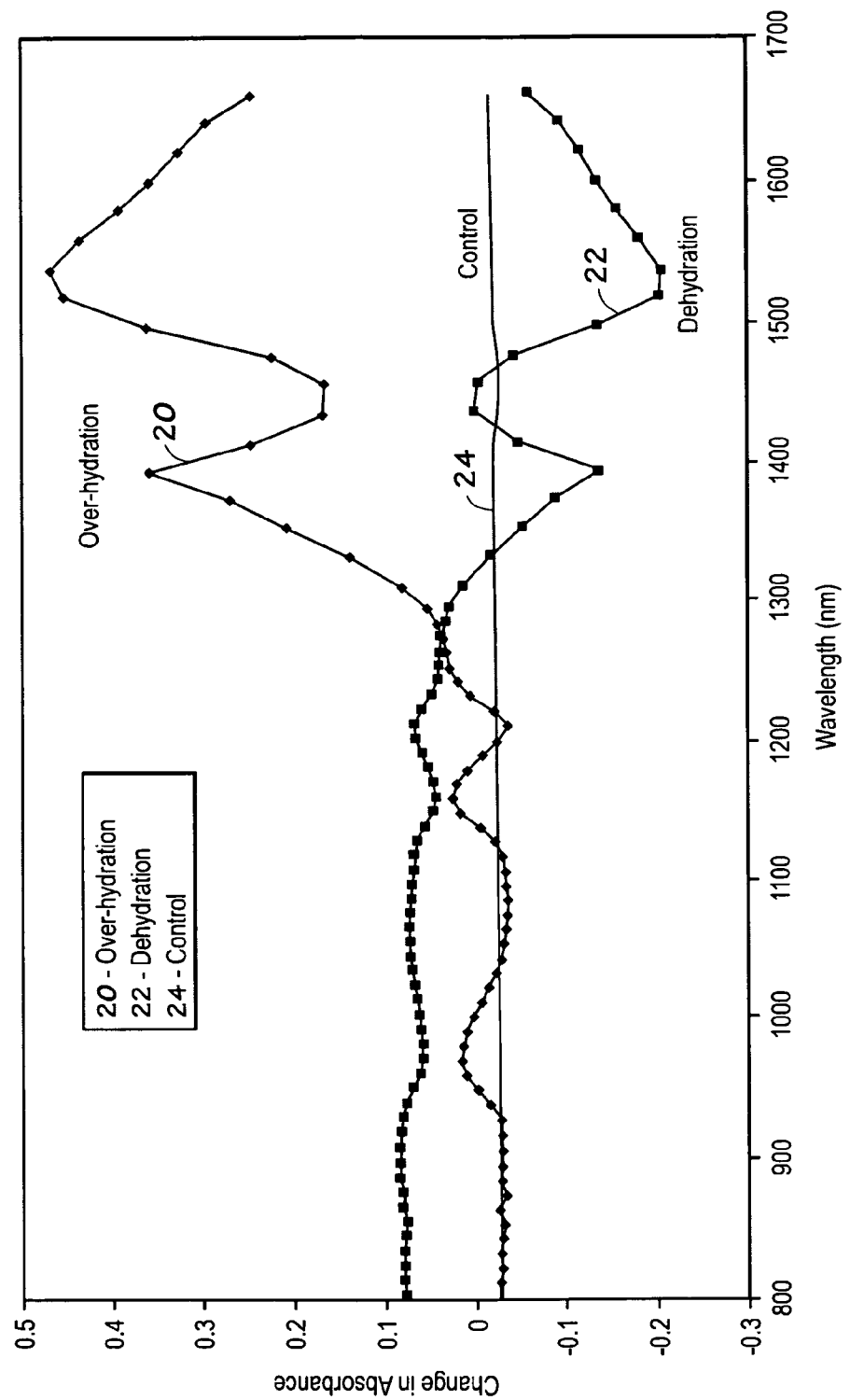
FIG. 3 illustrates a graph of the averaged spectral change induced by hydration change of piglets in vivo.

Difference spectra from 15 piglet hydration change experiments are shown in FIG. 3. The difference spectra are generated by subtracting the initial spectrum from the spectrum measured after a hydration change. The difference spectra are averaged according to the type of hydration change that was performed. Plot 20 illustrates the averaged spectra for five piglets which experienced over-hydration, plot 22 illustrates the averaged spectra of eight piglets which experienced dehydration, and plot 24 illustrates the averaged spectra of two piglets which served as control. Dehydration was accomplished by ultrafiltration of the blood over the course of six hours by approximately 9% of initial body weight.

A spectral broadening effect with over-hydration is manifested in the difference spectra as an increase in the tails of the 1450 nm water band relative to the center of the band. The difference spectra measured during dehydration experiments are remarkably symmetrical with the over-hydration difference spectra, showing a narrowing of the same absorbance band with dehydration. The control experiments, where no hydration change was performed, showed little variation in the spectra between the beginning and end of the experiment. Although only the averaged changes are shown in FIG. 3, the same bandwidth trend was observed in all individual piglet experimentations. The high reproducibility of the bandwidth trend observed across multiple piglets suggests that a simple measurement of absorption bandwidth may be useful as a hydration estimate.

Table 1 shows various possible combinations of wavelengths between 800 and 1600 nm which may be selected and used for correlating to the hydration index. Using only two wavelength bands, centered at 1450 and 1500 nm, with a 75 nm full-width half-max bandwidth, the hydration index can be predicted with a high correlation coefficient ($R^2$) and calibration error of approximately one percent. Therefore, using only these two wavelengths, the width of the 1450 nm water band on the long wavelength side can effectively be measured.

TABLE 1

Effect of Increasing number of wavelengths on prediction error.

| # λ's | $R^2$ | Err. (%) | $\lambda_1$ (nm) | $\lambda_2$ (nm) | $\lambda_3$ (nm) | $\lambda_4$ (nm) |
|---|---|---|---|---|---|---|
| 1 | 0.354 | 1.79 | 1650 | | | |
| 2 | 0.809 | 0.98 | 1500 | 1450 | | |
| 3 | 0.838 | 0.91 | 1550 | 1430 | 850 | |
| 4 | 0.887 | 0.76 | 1500 | 1450 | 1100 | 1070 |

Figure 4:
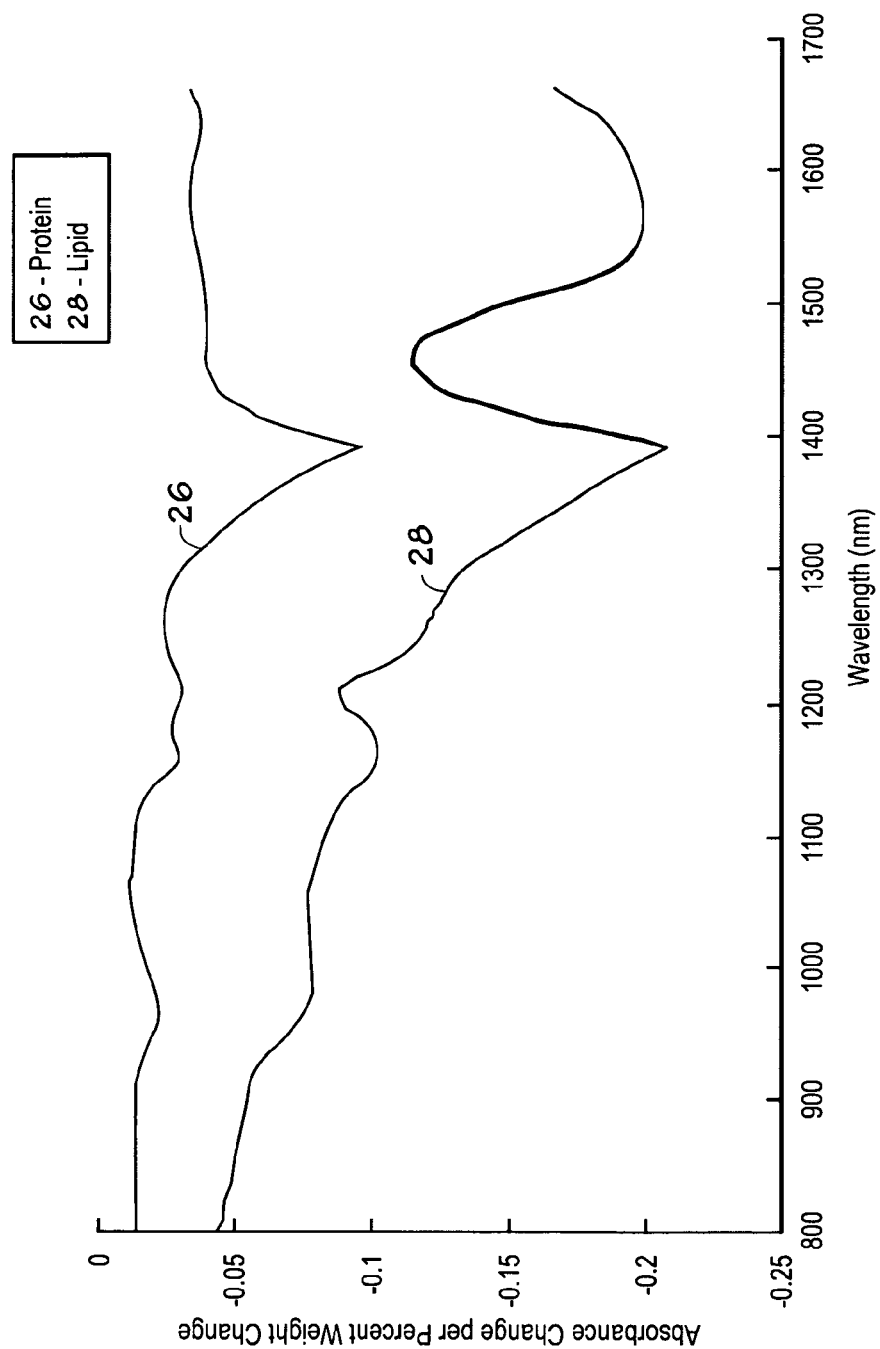
FIG. 4 illustrates a graph of the averaged spectral change induced by hydration of tissue phantoms.

The source of the water bandwidth variation due to hydration changes was investigated using tissue "phantoms." The phantoms were artificially constructed to mimic real tissue by selecting materials with similar constituents and optical properties to real tissue. The phantoms were constructed from varying proportions of water, protein, lipid, and scatterers, such as silicon oxide beads. FIG. 4 shows the average effect of increasing either the protein or lipid concentrations relative to the water concentration. The protein plot 26, illustrating the effect of increasing the concentration of protein relative to the water content, shows a much smaller effect on a percent weight basis relative to the lipid plot 28. The largest effect of increasing lipid concentration relative to water is a narrowing of the water band centered at 1450 nm. Importantly, it appears that the interaction effect between lipid and water effects both the long and short wavelength sides of the water band, whereas the interaction effect between protein and water effects primarily only the short wavelength side of the water band. On this basis, it should thereby be possible to separate the interaction effects due to protein and lipid on the water spectrum. For example, it may be possible to directly measure lean water fraction (or Hydration Index) by making 2 separate bandwidth measurements, one on the long wavelength side and another on the short wavelength side of the 1450 nm water absorption peak.

Figure 5:
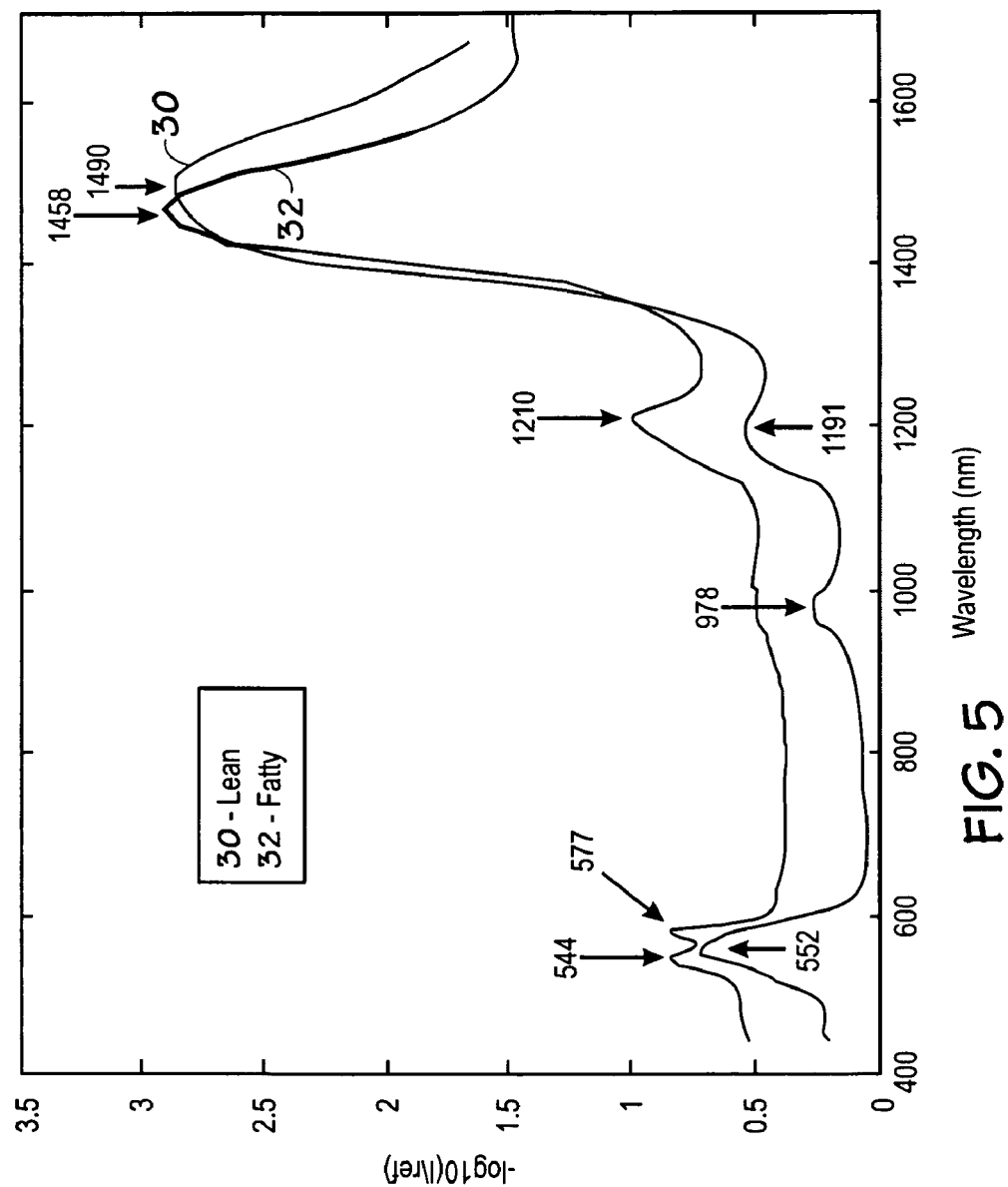
FIG. 5 illustrates a graph of the reflectance spectra of muscle and fat sides of a pork chop.

The tissue phantom results suggest that a major cause of the water band shift effect is interaction between water and lipid. In order to confirm this in real tissue, diffuse reflectance spectra of a pork chop were measured on a fatty portion and on a lean portion. The results, shown in FIG. 5, demonstrate that the interaction between lipid and water has the effect of narrowing and blue-shifting the water absorption peak at 1450 nm. Plot 30 illustrates the transmission spectrum of lean pork chop, while plot 32 illustrates the transmission spectrum of fatty pork chop. Plot 32 shows the spectrum of the fatty pork chop is narrower and blue-shifted as compared to plot 30 of the lean pork chop. Thus, the results shown in FIG. 5 confirm the "phantom" tests by demonstrating the narrowing of the water band centered at 1450 when lipid concentration is increased.

The hypothesized mechanism for the water bandwidth change with tissue hydration is interaction between water and surrounding tissue constituents (principally lipid and protein) leading to disruption of the hydrogen bonding network of liquid water. The broad width of the NIR absorbance bands of water at room temperature have previously been suggested to be due to the wide variety of hydrogen bonding interactions available to water. Evidence for this includes the observed narrowing and blue-shifting of the NIR water absorption peaks with increasing temperature. Various solutes and solvents have been classified as having either an ordering or disordering affect on water based on the width and peak position of NIR water bands. From the results discussed above, it is clear that both protein and lipid have a disordering effect on the hydrogen bonding in water, but with distinctive spectral signatures. Increasing the protein or lipid concentration relative to water will have a similar effect to increasing temperature of a pure water solution causing the width of NIR water bands to become narrower and the peak to shift to the blue.

In an exemplary embodiment, two light emitting diodes (LEDs) operating in the 1350-1650 nm spectral region, such as the 1450 and 1500 nm LEDs described above, are implemented with a detector, such as an InGaAs detector. The LEDs are selected to have a spectral bandwidth of approximately 75 nm or less. The LEDs are configured to transmit light into blood perfused tissue and the detector is configured to detect the light that is scattered and reflected by the tissue constituents and may be separated from the detector by 1-5 mm. For example, the LEDs may be positioned 2.5 mm from the detector.

In an alternative exemplary embodiment, a third LED emitting at about 1400 nm is used to provide a separate measurement of the absorption bandwidth on the short wavelength side of the 1450 nm peak. The short and long bandwidth measurements are then combined to provide an estimate of the lean water fraction in the tissue. For example, the logarithm of the reflectance measured from the three LEDs may be linearly combined to produce a quantity related to the ratio of water to protein (r) in the tissue. This ratio can then be related to the lean water fraction ($f^1_w$) by: $f^1_w = r/(1+r)$.

The amount of pressure applied to the blood perfused tissue should be limited to avoid exclusion of water from the sampled area. In an alternative embodiment, however, the pressure applied to the tissue may be varied and used as a means of separating "free" water from "bound" water, as disclosed in Method for Evaluating Extracellular Water Concentration in Tissue, by Clark R. Baker, Jr., U.S. Ser. No. 11/283,506, now U.S. Pat. No. 7,657,292, which is incorporated herein by reference.

Many other alternative embodiments, besides the combinations of LEDs shown in table 1, are also envisioned. One highly accurate method of determining the water bandwidth employs a tunable laser to scan across the water bands, for example. This method is disclosed in greater detail in Tunable Laser-based Spectroscopy System for Non-invasively Measuring Body Water Content, by Seungug Koh, U.S. Ser. No. 11/716,394, now U.S. Publication No. 2008/0220512, which is incorporated herein by reference. Other alternative light sources include vertical-cavity surface-emitting lasers (VCSELs) and broadband sources coupled with narrowband optical filters. Other methods for determining bandwidth, generally known to those skilled in the art of NIR spectroscopy, including scanning-grating spectroscopy, diode array spectroscopy, Fourier transform spectroscopy, and Hadamard transform spectroscopy may also be implemented.

Although measurement of the bandwidth of the water spectrum at 1450 nm has been discussed in detail herein, it will be appreciated that other water absorption bands may be used to achieve similar results. Specifically, measuring the spectral width of the water bands having peaks at 980, 1190, 1900, or 2350 nm may also be useful in determining a hydration index.

Figure 6A:
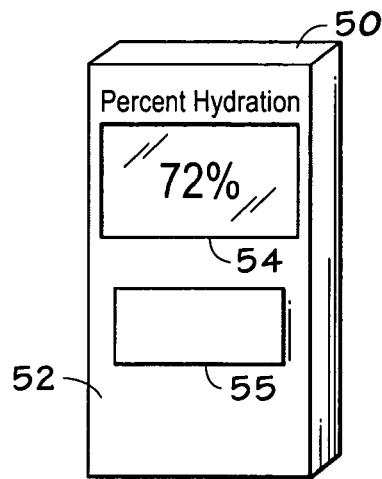
FIG. 6a illustrates the top side of a handheld system for measuring tissue hydration in accordance with an exemplary embodiment of the present invention.

Referring to FIG. 6a, an illustration of a system configured to measure tissue hydration in accordance with an exemplary embodiment of the present invention is shown and generally designated by the reference numeral 50. The system 50 may be configured as a single unit that can be carried with a user, nurse or doctor. The system 50 has a top side 52 with a display 54 configured to indicate the percent hydration of the tissue that is being probed. The top side 52 of the system 50 may have a keypad 55 that can allow a user to communicate with the system 50. For example the keypad 55 can be used to turn on and off the system 50, or to enter baseline values or other pertinent parameters. For example, baseline hydration values indicative of a certain condition such as dehydration or overhydration may be entered.

Figure 6B:
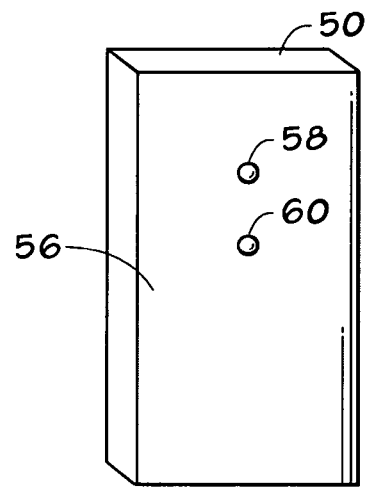
FIG. 6b illustrates the under side of the system of FIG. 6 in accordance with an exemplary embodiment of the present invention.

The underside 56 of the system 50 is illustrated in FIG. 6b. The underside 56 has an emitter 58 and a detector 60. The emitter 58 may be at least one device capable of emitting electromagnetic radiation in the 980 to 2350 nm spectral region. For example, the emitter 58 may be one or more LEDs operating at wavelengths indicated in Table 1 above. Alternatively, the emitter 58 may be a source capable of emitting across a broad range of wavelengths, such as a tunable laser. Light transmitted into the tissue of a patient is reflected and/or scattered by the various constituents of the tissue before arriving at a photoelectric detector 60. The detector 60 may be an InGaAS detector, or any other suitable photodetector capable of detecting at the wavelengths of light emitted by the emitter 58. The underside 56 may be opaque except for where the emitter 58 and detector 60 are located, since the opaque colorization helps to limit reflections as well as interference from light sources other than the emitter 58.

Figure 7:
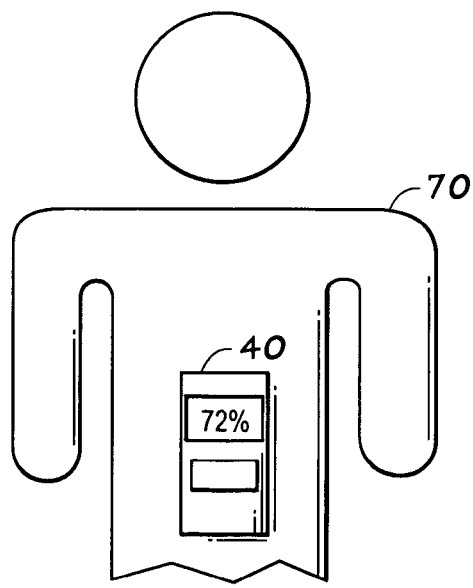
FIG. 7 illustrates using the system of FIG. 6a to estimate tissue hydration in accordance with an exemplary embodiment of the present invention.

The system 50 may take measurements from a single location on a patient's body and correlate the measurement to a whole body hydration index. Specifically, the system 50 may be placed along the centerline of the torso of a patient 70, as shown in FIG. 7 and a hydration index indicative of whole body hydration may be determined. In alternative applications, the system 50 may be configured to be placed on multiple locations of a patient's body to test for other conditions, such as edema, for example.

Figure 8:
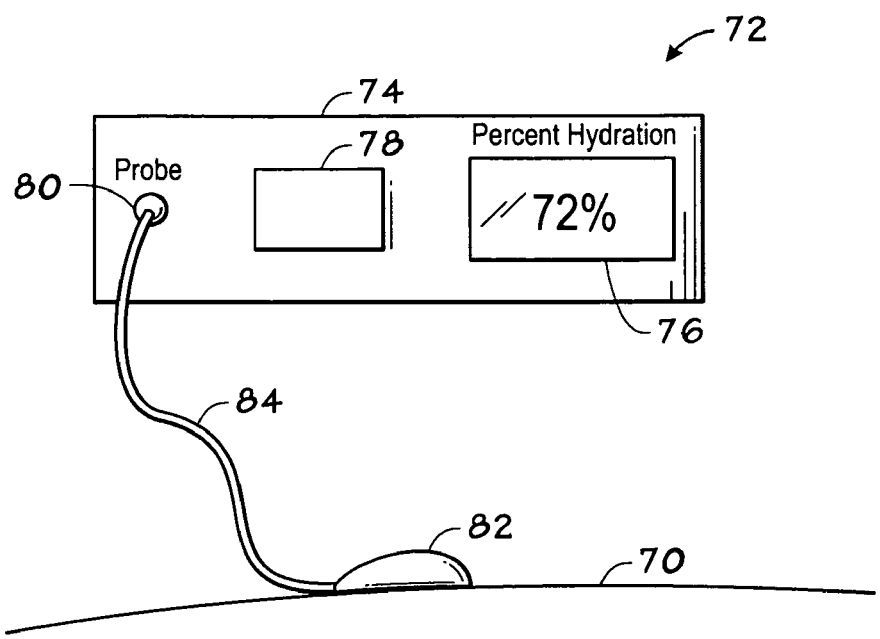
FIG. 8 illustrates a system for tissue hydration estimation in accordance with an alternative exemplary embodiment of the present invention.

A system showing an alternative exemplary embodiment is shown in FIG. 8, and is generally designated by the reference numeral 72. The system 72 has similar features to the system 50, but is intended to be placed on a desktop, shelf, or cart. The housing 74 of the system 72 is larger than that of the handheld embodiment and may be configured with additional features, such as increased memory space and/or expansion, for example. The system 72 has a display 76, a keypad 78 and a connector 80. The display 76 may be configured to indicate a hydration index measurement or other measured parameters. The keypad 78 may allow for users to input pertinent data, as discussed above. The connector 80 allows for a sensor 82 to communicate with the system 72 via a cable 84 or other means. The sensor 82 houses emitters and detectors, as described above, for taking spectral measurements. The spectral measurements are passed to the system 72 via the cable 84 for analysis and determination of hydration.

Figure 9:
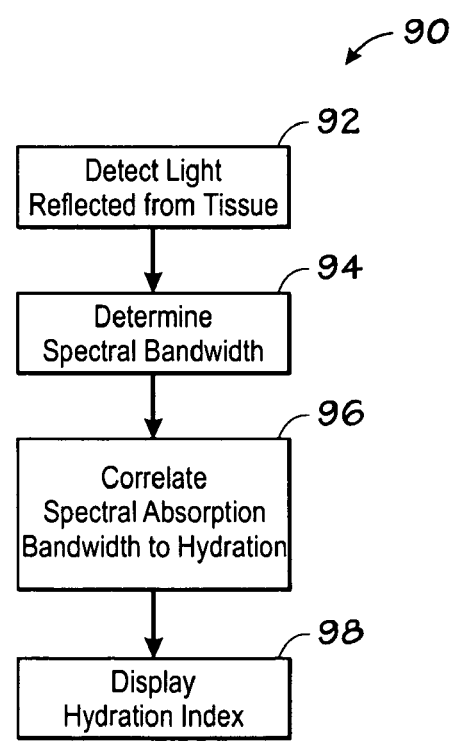
FIG. 9 is a flowchart illustrating a technique for measuring tissue hydration.

Turning to FIG. 9, a flowchart of an exemplary technique for determining fluid balance is illustrated and generally designated by the reference numeral 90. The technique begins by detecting light reflected from tissue, as indicated at block 92. As explained previously, a sensor can be placed along the centerline of the torso of the individual and transmit light into tissue. The tissue constituents of the tissue absorb, scatter and reflect the light. Light scattered and reflected by the tissue may be detected by a photodetector.

The spectral bandwidth of a water absorption band is determined by the detected light, as indicated at block 94. The spectral absorption bandwidth is correlated to the hydration of the tissue, as indicated at block 96. As discussed in detail above, the absorption bandwidth of water varies according to the relative concentration of tissue constituents. Specifically, over-hydration is indicated by a red shift and a broadening of the absorption bandwidth of water, while dehydration is indicated by a blue shift and a narrowing of the absorption bandwidth of water. Therefore, the measurement of the spectral absorption bandwidth allows for the determination of the hydration index.

The correlation between the spectral absorption bandwidth and the hydration index of the tissue is a direct correlation. Specifically, the absorption bandwidth in nanometers indicates a particular hydration index of the tissue. For example, an absorption bandwidth of 15 nm may indicate hydration level of 80%. In alternative embodiments, the correlation between the absorption bandwidth and hydration may be more complex. For example, in an alternative embodiment, the peak shift may be considered in combination with absorption bandwidth. In another embodiment, the absorption bandwidth may be measured separately on the short and long wavelength sides of the absorption peak. Additionally, in yet another alternative embodiment, patient specific parameters may be taken into consideration when determining the hydration level. For example, a patient's body fat percentage or body temperature may be entered and used to calibrate the correlation of between absorption bandwidth and the hydration level. The calibration may, for example, cause the correlation of absorption bandwidth to hydration to be scaled in accordance with the body fat percentage.

The hydration index, once determined, may be displayed, as indicated at block 98. The hydration index displayed may be used in determining whether or not an individual has a proper fluid balance. Specifically, the hydration index can indicate a dehydration or over-hydration state. The technique 90 may be repeated and a series of measurements may be made over time. The measurements may then be compared to determine if hydration trends are occurring such that there may be cause for alarm or to indicate a change in treatment may be necessary. Accordingly, the observed trend data can be used to determine if a patient is becoming dehydrated, for example.

The spectroscopic studies on piglets, discussed above, were conducted using a reflectance sensor with low-OH optical fibers to collect NIR spectra. A ring of 36 illumination fibers (400 µm core diameter, 0.37 NA) were arranged in a 5 mm diameter circle around 6 detection fibers (200 µm diameter, 0.22 NA). The sensor was attached to the tissue via an oval-shaped adhesive. The sensor was placed in contact with the tissue, but without applying pressure. Light was supplied to the illumination fibers by two 0.5 W tungsten filament bulbs. The detection fibers were arranged in a line for input into the NIR spectrometer. The NIR spectrometer consisted of a grating and a 256-element cooled InGaAs diode array and allowed the NIR spectrum to be measured with 18 nm resolution between 800 and 1600 nm.

In the studies, pre-anesthetic medication (telozol/atropine) was given intra muscularly 30 minutes prior to the induction of anesthesia. Each piglet was intubated and general anesthesia was induced using 2% isoflurane in oxygen. After induction, catheters were inserted into a central artery and vein, and a Foley catheter was surgically inserted into the bladder. General anesthesia was maintained by volume-controlled ventilation with isoflurane (2.0 vol %) delivered in 100% oxygen via veterinary anesthesia ventilator. The protocol allowed adjustments of inspired isoflurane concentration in the order of 1-2 vol % according to reactions to standardized noxious stimuli or changes in blood pressure and heart rate. Ventilation (volume-controlled) was adjusted to produce normo-capnia (arterial carbon dioxide level about 40 mmHg) based on repeated arterial blood gas analysis and end-tidal carbon dioxide monitoring.

The over-hydration experiments consisted of administration of 1 L of LRS in 20 minutes followed by 40 minutes of equilibration time. Additionally, a supplemental volume of LRS was given to compensate for the fluid lost from urine and blood sampling during the 40 minute equilibration period. This was repeated five times on each piglet so that a total of five liters of fluid was added over a five hour period. The under-hydration experiments consisted of removing 350 ml of body fluid from the piglets at hourly intervals over a four- or five-hour period via ultrafiltration.

At the completion of the experiment, the animals were euthanized and then frozen at −20° C. The entire carcass was them homogenized by grinding. To determine Hydration Index, several representative samples (approximately 1 g) of the homogenized carcass were accurately weighed to within 0.001 g. Samples were then lyophilized for at least three days and re-weighed. Lyophilization and weighing were repeated until no further weight change was observed. The fat content was then determined using a modification of the Folch method which excluded water from the extraction process. Briefly, an organic solvent was used to extract lipids from lyophilized tissue samples. The lipid-containing organic solvent was removed, washed with a solvent, and evaporated until only the lipid remained. Samples were re-weighed and the final weight was the fat-free, dry tissue weight. The hydration index was computed as the ratio of weight of water-to-the sum of the fat-free, dry tissue weight and the water weight. By combining the final whole carcass composition with continuous body weights, the hydration index could be determined throughout the experiment.

The solid tissue phantoms were created by mixing gelatin ("protein" component), corn oil ("lipid" component), scatterer (silicon oxide beads in water, 0.6-1.6 µm diameter, 2% solids content), and buffered water (deionized water 25 mM sodium carbonate, 50 mM sodium phosphate, 0.45% sodium chloride, pH 7.4). A two-level factorial design was constructed using lipid (5%, 15%), protein (15%, 20%), and scatterer (1%, 2%) as the variables. Temperature was treated as a fourth variable that was varied between two levels (25° C., 30° C.). A total of 16 optical measurements were made on the phantoms. Due to the factorial design of the experiment, the effect of each variable could be isolated simply by subtracting the average of all 8 samples at the low level of a given variable from the high level of the same variable.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of tissue hydration, but these techniques may also be utilized for the measurement and/or analysis of other analytes. The invention, therefore, is to cover all modifications, equivalents, and alternatives falling within the spirit and scope of the invention as defined by the following appended claims.

What is claimed is:

1. A method for determining tissue hydration comprising:
   detecting electromagnetic radiation scattered and reflected from living tissue;
   using the detected electromagnetic radiation to determine a spectral absorption bandwidth by measuring a width of an absorption band substantially centered about an absorption peak; and
   correlating the spectral absorption bandwidth to a tissue hydration index.

2. The method of claim 1, comprising determining peak shift and correlating peak shift and the spectral absorption bandwidth to the tissue hydration index.

3. The method of claim 1, comprising emitting electromagnetic radiation, wherein the emitting comprises using light emitting diodes (LEDs) operating in the near-infrared spectrum having a spectral bandwidth of less than approximately 75 nm.

4. The method of claim 3, comprising using LEDs having emission peaks at 1500 nm and 1450 nm.

5. The method of claim 4, comprising using an additional LED having an emission peak at 1400 nm, the method comprising combining measurements at the three wavelengths to provide an estimate of a lean water fraction in the tissue.

6. The method of claim 5, comprising:
   linearly combining the logarithm of the measurements at the three wavelengths to produce a quantity related to the ratio of water-to-protein, (r), in the tissue; and
   correlating the ratio to the lean water fraction, ($f^1_w$), by: $f^1_w = r/(1+r)$.

7. The method of claim 3, comprising using LEDs having emission peaks at 1550 nm, 1450 nm and 1400 nm.

8. The method of claim 3, comprising using LEDs having emission peaks at 1550 nm, 1430 nm and 850 nm.

9. The method of claim 3, comprising using LEDs having emission peaks at 1500 nm, 1450 nm, 1100 nm, and 1070 nm.

10. The method of claim 1, comprising emitting electromagnetic radiation, wherein the emitting comprises using at least one tunable laser.

11. The method of claim 1, comprising emitting electromagnetic radiation, wherein the emitting comprises using vertical-cavity surface-emitting lasers.

12. The method of claim 1, comprising emitting electromagnetic radiation, wherein the emitting comprises using a broadband source coupled with narrowband optical filters.

13. The method of claim 1, comprising emitting electromagnetic radiation, wherein the emitting comprises implementing NIR spectroscopy.

14. The method of claim 13, comprising using scanning-grating spectroscopy.

15. The method of claim 13, comprising using diode array spectroscopy.

16. The method of claim 1, wherein using the detected electromagnetic radiation to determine spectral absorption bandwidth comprises measuring absorption bandwidth separately on a short wavelength side and a long wavelength side of the absorption peak.

17. The method of claim 1, correlating the spectral absorption bandwidth to the tissue hydration index comprises calibrating the correlation based on a patient specific parameter.

18. The method of claim 1, wherein detecting electromagnetic radiation comprises using an InGaAs detector.

19. The method of claim 3, comprising using at least two LEDs having emission peaks spaced 25 to 250 nm apart in the 1800 to 2100 nm region of the spectrum.

20. The method of claim 1, wherein the absorption band comprises a water absorption band, and the spectral absorption bandwidth comprises the width between a short wavelength side and a long wavelength side of the absorption peak at approximately half intensity of a maximum intensity of the absorption peak.

21. A system for measurement of living tissue comprising:
   a sensor unit configured to emit and detect electromagnetic radiation; and
   a hydration index unit coupled to the sensor unit and configured to determine a spectral absorption bandwidth by measuring a width of an absorption band substantially centered about an absorption peak and to correlate the spectral absorption bandwidth to living tissue hydration.

22. The system of claim 21, comprising a display configured to output a tissue hydration estimation.

23. The system of claim 21, wherein the sensor unit comprises at least one emitter and at least one detector.

24. The system of claim 23, wherein the at least one emitter operates in the 1300 nm to 1650 nm spectral region.

25. The system of claim 23, wherein the at least one emitter comprises a first LED operating at 1500 nm having a spectral bandwidth of less than 75 nm and a second LED operating at 1450 nm having a spectral bandwidth of less than 75 nm.

26. The system of claim 25, wherein the at least one emitter comprises a third LED operating at 1400 nm having a spectral bandwidth of 75 nm or less.

27. The system of claim 23, wherein the at least one detector comprises an InGaAs photodetector.

28. The system of claim 21, wherein the hydration index unit is configured to determine peak shift and correlate peak shift and spectral absorption bandwidth to hydration.

29. The system of claim 21, wherein the hydration index unit and the sensor unit are integrated into the same housing.

30. The system of claim 21, wherein the sensor unit comprises a tunable laser.

31. The system of claim 21, wherein the sensor comprises a broadband source coupled with narrowband optical filters.

32. The system of claim 21, wherein the sensor comprises a vertical-cavity surface-emitting laser.

33. The system of claim 21, wherein the sensor comprises a scanning-grating spectroscope.

34. The system of claim 21, wherein the sensor comprises a diode array spectroscope.

35. The system of claim 21, wherein the hydration index unit is configured to determine spectral absorption bandwidth by measuring absorption bandwidth separately on a short wavelength side and a long wavelength side of an absorption peak.

36. The system of claim 21, wherein the hydration index unit is configured to correlating the spectral absorption bandwidth to living tissue hydration by calibrating the correlation based on a patient specific parameter.

37. The system of claim 21, wherein the absorption band comprises a water absorption band, and the spectral absorption bandwidth comprises the width between a short wavelength side and a long wavelength side of the absorption peak at approximately half intensity of a maximum intensity of the absorption peak.

* * * * *